US008968327B2

(12) United States Patent
Klotz et al.

(10) Patent No.: US 8,968,327 B2
(45) Date of Patent: Mar. 3, 2015

(54) INSTRUMENTATION FOR RECORDING AND REPLICATING ORTHOPAEDIC IMPLANT ORIENTATION

(71) Applicant: DePuy Synthes Products, LLC, Raynham, MA (US)

(72) Inventors: Conrad Klotz, Nappanee, IN (US); Daren Deffenbaugh, Winona Lake, IN (US); Trent Wilkinson, Larwill, IN (US); Edmund Frazee, Cromwell, IN (US)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

(21) Appl. No.: 14/330,500

(22) Filed: Jul. 14, 2014

(65) Prior Publication Data
US 2014/0324174 A1   Oct. 30, 2014

Related U.S. Application Data

(62) Division of application No. 14/045,874, filed on Oct. 4, 2013, now Pat. No. 8,808,306, which is a division of application No. 13/597,840, filed on Aug. 29, 2012, now Pat. No. 8,585,711, which is a division of application No. 10/879,261, filed on Jun. 29, 2004, now Pat. No. 8,273,093.

(51) Int. Cl.
A61B 17/58    (2006.01)
A61B 17/60    (2006.01)
(Continued)

(52) U.S. Cl.
CPC ................................. A61F 2/4014 (2013.01)
USPC ........................................................ 606/102

(58) Field of Classification Search
USPC .................................... 606/91, 102, 99, 87
See application file for complete search history.

(56) References Cited

U.S. PATENT DOCUMENTS 4,003,095 A    1/1977  Gristina
4,676,797 A    6/1987  Anapliotis et al.
(Continued)

FOREIGN PATENT DOCUMENTS

DE    4445892 A1    6/1996
DE    19509037 C1   9/1996
(Continued)

OTHER PUBLICATIONS

Australian Search Report in Australian application AU2005247033, mailed Apr. 23, 2010 (2 pages).
(Continued)

Primary Examiner — Sameh Boles
(74) Attorney, Agent, or Firm — Maginot, Moore & Beck LLP

(57) ABSTRACT

A system for preparing an implant for implantation includes a trial implant including a first dialable component and a datum, a final implant including a second dialable component, and an instrument including (i) a base assembly configured to support the trial implant so that the datum is in a predetermined orientation, (ii) a fixture supported on the base assembly, the fixture including a domed element, and an alignment tool configured to engage the first dialable component when the trial implant is supported by said base assembly, and (iii) a locking assembly including a guide member defining a spherical surface for nested engagement with said domed element, the locking assembly configured to record the angular orientation of said alignment tool relative to said fixture with said alignment tool engaged with the first dialable component, and to replicate the recorded angular orientation with the alignment tool and a second dialable component.

20 Claims, 5 Drawing Sheets

(51) Int. Cl.
*A61F 2/00* (2006.01)
*A61F 2/40* (2006.01)

(56) References Cited

U.S. PATENT DOCUMENTS

| | | | |
|---|---|---|---|
| 4,822,370 A | 4/1989 | Schelhas | |
| 5,076,541 A | 12/1991 | Daghe et al. | |
| 5,080,685 A | 1/1992 | Bolesky et al. | |
| 5,314,479 A | 5/1994 | Rockwood, Jr. et al. | |
| 5,358,526 A | 10/1994 | Tornier | |
| 5,370,706 A | 12/1994 | Bolesky et al. | |
| 5,702,457 A | 12/1997 | Walch et al. | |
| 5,725,597 A | 3/1998 | Hwang | |
| 5,741,335 A | 4/1998 | Gerber et al. | |
| 5,743,898 A | 4/1998 | Bailey et al. | |
| 5,910,143 A | 6/1999 | Cripe et al. | |
| 6,083,263 A | 7/2000 | Draenert et al. | |
| 6,197,062 B1 | 3/2001 | Fenlin | |
| 6,203,575 B1 | 3/2001 | Farey | |
| 6,206,925 B1 | 3/2001 | Tornier | |
| 6,228,120 B1 | 5/2001 | Leonard et al. | |
| 6,283,999 B1 | 9/2001 | Rockwood, Jr. | |
| 6,328,748 B1 | 12/2001 | Hennig | |
| 6,361,566 B1 | 3/2002 | Al-Hafez | |
| 6,478,500 B1 | 11/2002 | Farenholtz | |
| 6,558,425 B2 | 5/2003 | Rockwood, Jr. | |
| 6,620,197 B2 | 9/2003 | Maroney et al. | |
| 6,626,946 B1 | 9/2003 | Walch et al. | |
| 6,673,114 B2 | 1/2004 | Hartdegen et al. | |
| 6,736,851 B2 | 5/2004 | Maroney et al. | |
| 6,736,852 B2 | 5/2004 | Callaway et al. | |
| 6,749,637 B1 | 6/2004 | Bahler | |
| 6,776,799 B2 | 8/2004 | Ball et al. | |
| 6,863,690 B2 | 3/2005 | Ball et al. | |
| 6,953,478 B2 | 10/2005 | Bouttens et al. | |
| 7,192,449 B1 | 3/2007 | McQueen et al. | |
| 7,238,207 B2 | 7/2007 | Blatter et al. | |
| 7,431,736 B2 | 10/2008 | Maroney et al. | |
| 2001/0041940 A1 | 11/2001 | Pearl | |
| 2001/0053935 A1 | 12/2001 | Hartdegen et al. | |
| 2002/0016634 A1 | 2/2002 | Maroney et al. | |
| 2003/0014112 A1 | 1/2003 | Ralph et al. | |
| 2003/0040802 A1 | 2/2003 | Errico et al. | |
| 2003/0097183 A1 | 5/2003 | Rauscher et al. | |
| 2004/0002765 A1 | 1/2004 | Maroney et al. | |
| 2004/0010261 A1 | 1/2004 | Hoag et al. | |
| 2004/0030400 A1 | 2/2004 | Horber | |
| 2004/0064142 A1 | 4/2004 | Ball et al. | |
| 2004/0064188 A1 | 4/2004 | Ball et al. | |
| 2004/0064189 A1 | 4/2004 | Maroney et al. | |
| 2004/0122440 A1* | 6/2004 | Daniels et al. | 606/102 |
| 2004/0167629 A1 | 8/2004 | Geremakis et al. | |
| 2005/0113931 A1 | 5/2005 | Horber | |
| 2005/0143829 A1 | 6/2005 | Ondrla et al. | |
| 2005/0149050 A1 | 7/2005 | Stifter et al. | |
| 2005/0187637 A1 | 8/2005 | Karrer et al. | |
| 2005/0251263 A1 | 11/2005 | Forrer et al. | |
| 2005/0288681 A1 | 12/2005 | Klotz et al. | |
| 2006/0142872 A1 | 6/2006 | Klotz et al. | |
| 2007/0078519 A1 | 4/2007 | Klotz | |
| 2007/0112430 A1 | 5/2007 | Simmen et al. | |
| 2012/0323250 A1 | 12/2012 | Klotz et al. | |
| 2014/0039508 A1 | 2/2014 | Klotz et al. | |

FOREIGN PATENT DOCUMENTS

| | | |
|---|---|---|
| DE | 19951141 A1 | 5/2001 |
| DE | 10123517 C1 | 11/2002 |
| DE | 202005020876 U1 | 10/2006 |
| EP | 0549480 A1 | 6/1993 |
| EP | 0679375 A1 | 11/1995 |
| EP | 0712617 A1 | 5/1996 |
| EP | 0715836 A1 | 6/1996 |
| EP | 0931522 A1 | 7/1999 |
| EP | 1186278 A2 | 3/2002 |
| EP | 1314407 A1 | 5/2003 |
| EP | 1321114 A1 | 6/2003 |
| EP | 1393697 A1 | 3/2004 |
| EP | 1402856 A1 | 3/2004 |
| EP | 1681037 A2 | 7/2006 |
| EP | 1769776 A1 | 4/2007 |
| FR | 2731612 A1 | 9/1996 |
| JP | 2004512922 A1 | 4/2004 |
| WO | 9303688 A1 | 3/1993 |
| WO | 0122905 A1 | 4/2001 |
| WO | 0239932 A1 | 5/2002 |
| WO | 03096870 A2 | 11/2003 |
| WO | 03096939 A1 | 11/2003 |

OTHER PUBLICATIONS

Australian Search Report in Australian application AU2005246996, mailed Apr. 27, 2010 (3 pages).
Australian Search Report in Australian application AU2006225167, mailed Mar. 22, 2011 (2 pages).
European Search Report in European application EP05257963.8, mailed Dec. 20, 2007 (5 pages).
European Search Report in European application EP05257964.6, mailed Dec. 20, 2007 (8 pages).
European Search Report in European application EP06255073.6, mailed Jan. 5, 2007 (8 pages).
European Search Report in European application EP09162325.6, mailed Oct. 2, 2009 (6 pages).
European Search Report in European application EP10178881.8, mailed Mar. 10, 2011 (5 pages).
European Search Report in European application EP10178895.8, mailed Dec. 14, 2010 (7 pages).
Japanese Office Action in Japanese application JP2005-378997, mailed Feb. 9, 2010 (12 pages including translation).
Japanese Office Action in Japanese application JP2006-267228, mailed Oct. 5, 2010 (4 pages).
The McElroy Translation Company, English translation of German Patent No. DE 101 23 517 C1, dated Jan. 2006 (20 pages).
Japan Patent Office, Notification of Reasons for Refusal (Translation) associated with patent application 2009-138953, mailed May 7, 2013 (4 pages).

* cited by examiner

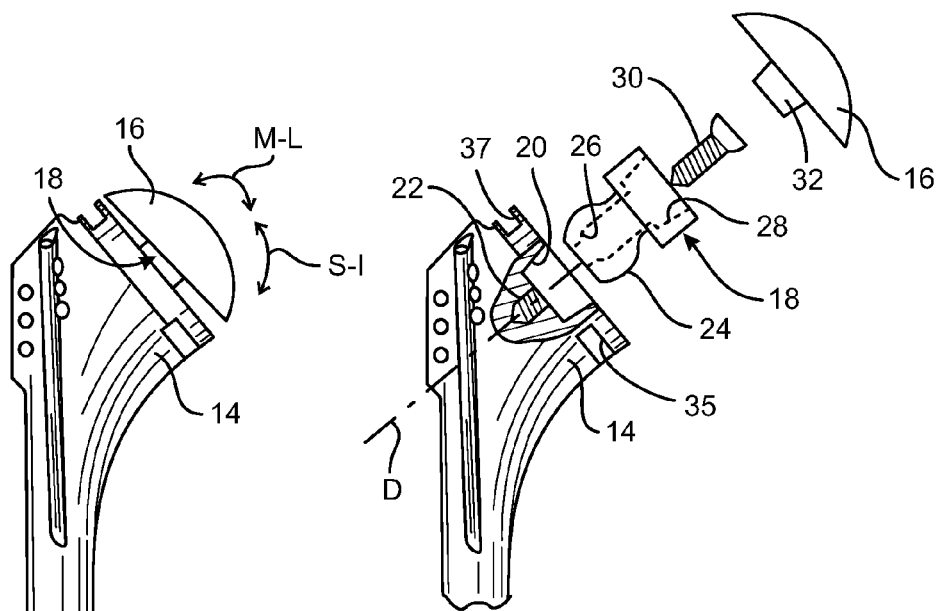
FIG. 2
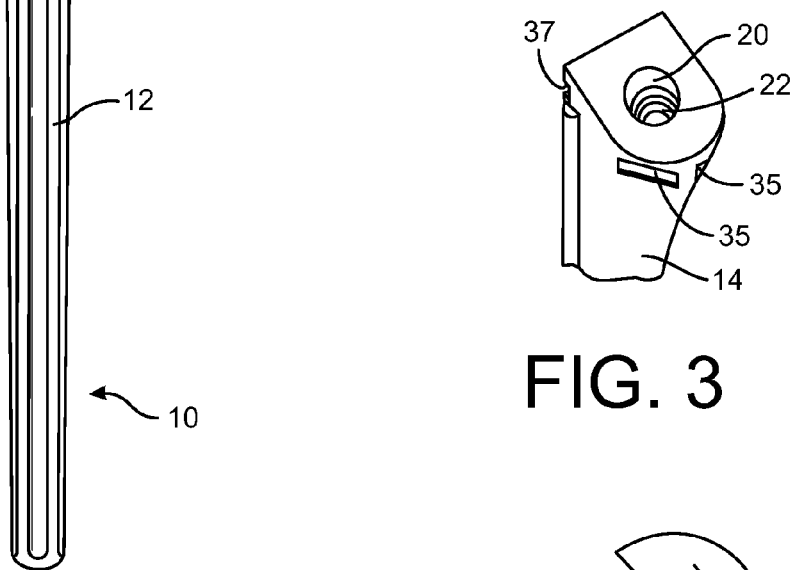
FIG. 1
FIG. 3
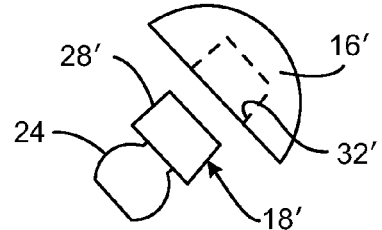
FIG. 2A

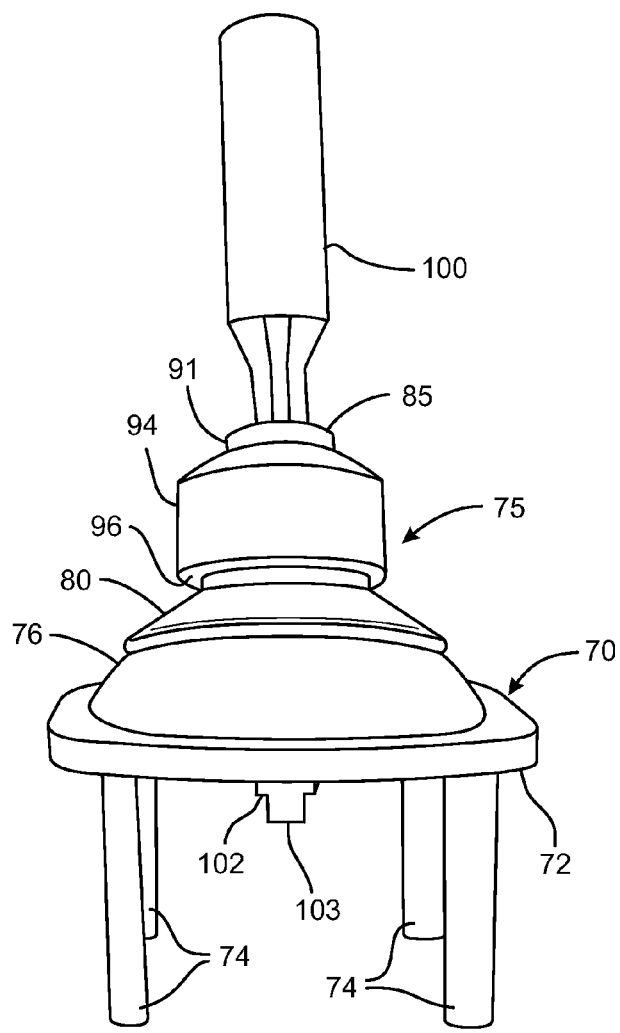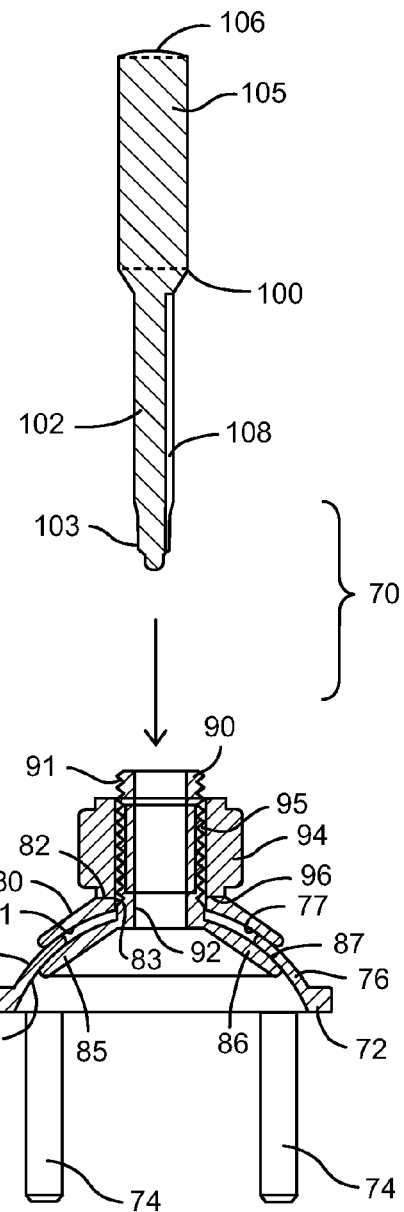
FIG. 9
FIG. 10

INSTRUMENTATION FOR RECORDING AND REPLICATING ORTHOPAEDIC IMPLANT ORIENTATION

This application is a divisional of U.S. application Ser. No. 14/045,874 filed Oct. 4, 2013, now U.S. Pat. No. 8,808,306 which issued Aug. 19, 2014, which is a divisional of U.S. application Ser. No. 13/597,840 filed Aug. 29, 2012, now U.S. Pat. No. 8,585,711 which issued Nov. 19, 2013, which is a divisional of U.S. application Ser. No. 10/879,261, filed Jun. 29, 2004, now U.S. Pat. No. 8,273,093 which issued Sep. 25, 2012, the entire contents of which are each herein incorporated by reference.

FIELD

The present disclosure relates to prosthetic devices particularly shoulder prostheses and, more particularly, to a method and apparatus for replication of angular position of a humeral head of a shoulder prosthesis.

BACKGROUND INFORMATION

The state of the prosthetic shoulder market has progressed such that a surgeon generally approaches shoulder replacement surgery according to one of two strategies. One strategy is to perform the shoulder replacement surgery in accordance with a manufacturer's shoulder prosthesis or shoulder prosthesis product line. Particularly, a surgeon is provided with instrumentation and technique guidelines for the particular shoulder prosthesis or prosthesis line. The guidelines and/or instrumentation direct or dictate the angle of humeral head resection for the implant (prosthesis). This angle is in relation to the humeral intramedullary (IM) canal and is designed to match an optimum set of angles already present in the design of the prosthesis.

Another approach is to perform the shoulder replacement surgery in accordance with the patient's anatomy. Particularly, the humeral head is resected according to angles perceived to be "anatomic" in the opinion of the surgeon, not according to angles already present in the prosthesis itself. With this approach, the prosthesis is designed so that its configuration is intraoperatively adjustable. This allows the prosthesis to be adjustable in situ so that it can match the bony preparation.

Even with respect to these two divergent manners of surgical strategy, a common problem in shoulder surgery is matching the humeral resection angle across the articular margin to the predetermined angle designed into the prosthesis. This angle may include the angle between a prosthetic collar and the diaphyseal section of the stem. In the case of a collarless stem, the angle may inscribe the difference between the longitudinal axis of the stem and the inferior surface of the prosthetic head. It is considered optimal for fixation and biomechanics if the resected angle and the angle of the prosthesis are identical, thereby allowing intimate contact between the superior surface of resected bone and the inferior surface of the implant.

Moreover, the angular version in which the prosthesis is implanted will have a significant impact on the biomechanics of the prosthetic joint. Currently, most shoulder prosthesis systems on the market dictate the varus/valgus angle of the bone cut. This strategy does not allow the surgeon to intraoperatively match the implant to the patient's biomechanics after the prosthesis has been trialed, much less implanted. There are two known products currently marketed that attempt to resolve at least one of the above-noted issues. First, the Tornier-Aequalis system provides a modular junction within the metaphyseal region of the stem which allows a small block between the stem and humeral head to be interchanged. This block is available in multiple angles, thus allowing the surgeon to select the block that best fits the bony anatomy as resected. This system, however, has two primary weaknesses. First, the use of modular blocks obviously forces the design to only allow angular adjustments in finite increments. Second, the need to adjust the angle through modular blocks forces the surgeon to remove the stem, change out a component, and reset the stem.

A second product currently marketed provides a humeral head that is infinitely adjustable in varus/valgus and anterior/posterior angles relative to the stem portion of the prosthesis. This is accomplished through a spherical shaped protrusion on the superior surface of the stem that fits into a spherical recess in the humeral head. These mating surfaces allow the head to be articulated about the stem, thus allowing adjustable positioning of the head. The head can be locked in a position relative to the stem. This solution provides the ability to adjust the neck-shaft angle as well as the version through flexibility in the anterior/posterior angle. The locking mechanism, however, is sub-optimal since it requires the turning of a locking screw that has its head facing lateral and inferior, for which there is no access once the stem has been cemented. This eliminates the ability to adjust head position on the fly, and forces a total revision if articular surfaces ever need to be revised. Lastly, the protrusion on the humeral stem even when the humeral head is not in place limits the surgeon's access to the glenoid in preparation for a glenoid replacement.

It should be appreciated that it is desired to have a prosthesis that is intraoperatively adjustable so that it can match the bony preparation. One such prosthesis that has attempted to provide this design feature provides a complicated and cumbersome jig to permit replication of the head angular position between the trial prosthesis and the final implant. One problem with this jig is that the head position is taken directly from the long axis of the humeral stem. Thus, the trial and implant stems are required to adjust and replicate this position. This means that the system has a large number of components to handle, and the position cannot be adjusted with the stem in vivo. Another problem is that the jig itself is a quite complicated table-top device. The jig includes an adjustment gage and a triplanar disc that must be manipulated to effect replication of the head orientation between trial and final implant.

With a shoulder prosthesis that allows a surgeon to adjust the angular position of the humeral head (i.e. adjust the articular surface of the humeral head relative to the humeral stem/component and/or bone) a method must be available for trialing the prosthesis. When the trial prosthesis is implanted, several adjustments can be made to set the angular position of the prosthetic head relative to the humeral stem. A means must be available for transferring the settings obtained during the trialing process to the final implant.

What is thus needed in view of the above is a better method for trialing a shoulder prosthesis, and more particularly for replicating the orientation of the trial implant components in the final implant. There is also a need for a replication system that is quick and easy to operate, as well as for a system that can be utilized with implants utilizing locking taper fixation.

SUMMARY

These and other needs are met by the present inventive recording and replication instrumentation that is capable of replicating the orientation of a dialable component of an implant relative to the bone engaging component of the implant. For instance, the present invention has particular value in the preparation of a final humeral implant having a stem configured for fixation within the humerus bone and a spherical head that is "dialably" mounted to the stem—i.e., is adjustably mounted so the three-dimensional angulation of the head can be adjusted as necessary for the particular patient anatomy.

A system for preparing an implant for implantation in one embodiment includes a trial implant including a first dialable component and a datum, a final implant including a second dialable component, and an instrument including (i) a base assembly configured to support the trial implant so that the datum is in a predetermined orientation, (ii) a fixture supported on the base assembly, the fixture including a domed element, and an alignment tool configured to engage the first dialable component when the trial implant is supported by said base assembly, and (iii) a locking assembly including a guide member defining a spherical surface for nested engagement with said domed element, the locking assembly configured to record the angular orientation of said alignment tool relative to said fixture with said alignment tool engaged with the first dialable component, and to replicate the recorded angular orientation with the alignment tool and a second dialable component.

The instrumentation contemplated by the present invention includes a base assembly for supporting the stem of a trial implant and a final implant, and a replication fixture that is supported on the base assembly, preferably so that it can be removed. The base assembly includes means for supporting the stem of an implant with a pre-determined datum in a pre-determined orientation. The same datum is used between the trial and final implants so that the configuration of the implant can be accurately repeated. The base assembly can include a clamp arrangement for clamping the implant stem in at least two degrees of freedom, and preferably in the medial-lateral, superior-inferior and anterior-posterior directions. The stem of the implant can include an array of notches or grooves that are engaged by clamp elements of the base assembly to fix the stem in those degrees of freedom.

The replication assembly is supported by several legs that are fixed to the base assembly or most preferably are removably fit within corresponding recesses in the base assembly. The replication assembly includes a guide member that supports an alignment tool. The alignment tool is configured to engage the dialable aspect of the implant so that the tool "records" the angular orientation of the dialable aspect relative to the datum. A locking mechanism locks the position of the guide member so that the alignment tool can be removed and replaced when a final implant is substituted in the base assembly. The alignment tool can then be used to position the dialable aspect of the final implant. In one embodiment, the alignment tool is an impaction tool to impact the dialable aspect within the implant stem to lock the components together at the replicated orientation.

In accordance with one embodiment of the invention, a method is provided for preparing an implant for implantation within a joint. The implant includes a stem for implantation within a bone and a dialable component mounted to the stem. In certain embodiments, the dialable component can include a head configured to engage an opposing portion of the joint, and a mounting assembly configured to fix the head to the stem in variable angular orientations to fit the joint anatomy. The inventive method comprises the steps of placing a stem of a trial implant within a bone of the joint, positioning a dialable component on the stem of the trial implant within the joint, using a jig to record an orientation of the dialable component relative to a pre-determined datum on the trial implant, and using the same jig to replicate the orientation for a dialable component of a final implant relative to the same datum on the final implant.

In certain aspects of the invention, the positioning step includes fixing the position of the trial dialable component relative to the datum of the trial implant, and the recording step includes supporting the trial implant within the jig with the datum in a predetermined orientation. The recording step can further include fixing the trial implant within the jig, using the jig to guide an alignment tool to engage the dialable component of the trial implant, and locking the angular orientation of the alignment tool relative to the jig when the alignment tool is in engagement with the dialable component.

The replicating step may include fixing a final implant within the same jig, using the jig to guide an alignment tool along the angular orientation obtained in the locking step, and manipulating the dialable component of the final implant and the alignment tool until the alignment tool engages the dialable component of the final implant. In certain embodiment, the replicating step includes fixing the dialable component to the stem of the final implant. This fixing step is preferably performed using the alignment tool. For instance, where the mounting assembly of the final implant forms a press-fit engagement between the stem and the dialable component, the step of fixing the dialable component includes impacting the alignment tool to impact the dialable component into press-fit engagement with the stem of the final implant.

In certain embodiments, the dialable component includes a mounting assembly for mounting a head to the stem of the implant and the mounting assembly includes a fixed component fixed in the stem and a dialable component capable of assuming various angular orientations relative to the fixed component. In accordance with these embodiments, the datum is a predetermined axis passing through the fixed component. For example, the fixed component is a tapered bore and the datum is the centerline axis through the bore.

The present invention further contemplates an instrument for recording the position of a dialable component of an implant relative to a predetermined datum on a stem of the implant configured to be engaged in a bone. This instrument comprises, in certain embodiments, a base assembly for supporting the stem with the datum in a predetermined orientation, a fixture removably mountable on the base assembly when supporting the stem, the fixture including an alignment tool for engaging the dialable component of the implant when the stem is supported by the base assembly, and a locking assembly for locking the angular orientation of the alignment tool relative to the fixture with the alignment tool aligned with the dialable component so that the alignment tool defines an angular orientation of the dialable component relative to the datum.

The base assembly includes an assembly configured to clamp the stem to the base assembly. Preferably, the assembly is a clamp assembly that is self-centering so that it is configured to center the stem relative to the base assembly in at least two degrees of freedom. In one feature of the invention, the clamp assembly includes a v-shaped clamping element configured to engage angled grooves defined in the stem.

In one feature of the inventive instrument, the locking assembly is configured to permit removal of the alignment tool after the angular orientation has been locked. The fixture may include a domed element defining an opening for extension of the alignment tool therethrough, and the locking assembly includes a guide member defining a bore for extension of the alignment tool therethrough, the guide member defining a spherical surface for nested engagement with the domed element. In some embodiments, the guide member includes a post projecting from the spherical surface, the post defining the bore and the opening is sized to receive the post therethrough to permit movement of the guide member relative to the domed element in at least two degrees of freedom. Preferably, the permitted movement relative to the domed element is a spherical angle. The post of the guide member includes external threads and the locking assembly further includes a nut configured to engage the external threads. A washer can be provided between the nut and the domed element with the dome surface disposed between the washer and the spherical surface of the guide member.

Preferably, the fixture includes at least one support leg and the base assembly defines at least one recess corresponding to the at least one support leg for removable engagement of the leg therein. With this feature, the fixture can be removed to permit placement in or removal of an implant in the base assembly.

It is one object of the invention to provide a system and method for readily and easily preparing a final implant that accurately duplicates the orientation or configuration of a trial implant that has been used to determine the proper implant configuration. Another object resides in features of the invention that ensure virtually identical replication of the position of a dialable component of an orthopaedic implant.

One benefit of the invention is that the inventive system and method permits use of standard trial and final implants. Another benefit is that the final implant can be prepared apart from the patient without sacrificing an optimal anatomical fit for the implant, which can be especially valuable where locking tapers are used.

BRIEF DESCRIPTION OF THE FIGURES

FIG. 1 is side elevational view of an exemplary shoulder prosthesis for use with the present invention.

FIG. 2 is an exploded partial cross-sectional view of a portion of the shoulder prosthesis shown in FIG. 1.

FIG. 2a is an exploded partial view of a modified head and dialable component for use with the prosthesis shown in FIGS. 1-2.

FIG. 3 is a top perspective view of a portion of the shoulder prosthesis shown in FIG. 1.

FIG. 9 is a side perspective view of a replication fixture for the recording and replication instrument in accordance with one embodiment of the present invention.

FIG. 10 is an exploded partial cross-sectional view of the replication fixture shown in FIG. 9.

DESCRIPTION OF THE PREFERRED EMBODIMENTS

Figure 4:
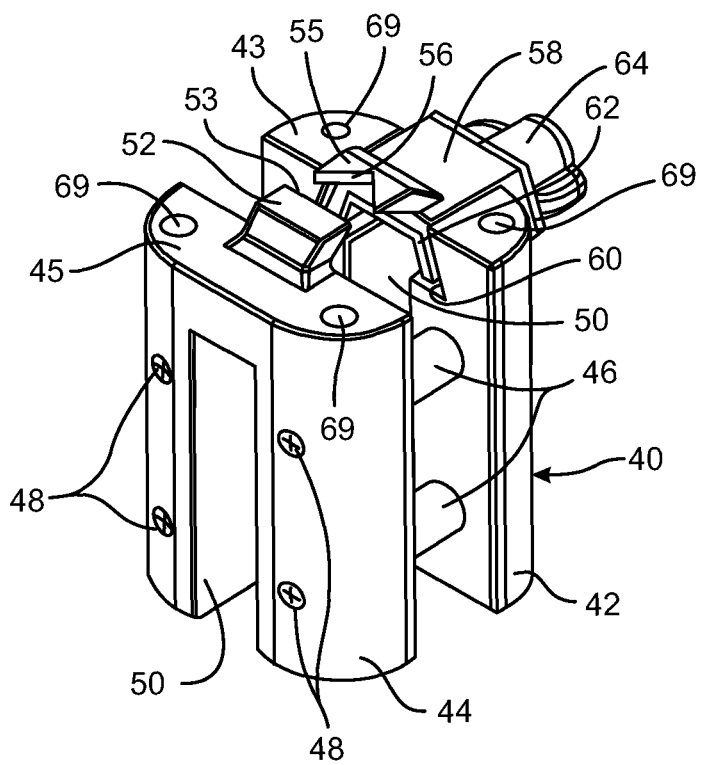
FIG. 4 is a top perspective view of a base assembly for a recording and replication instrument in accordance with one embodiment of the present invention.
Figure 5:
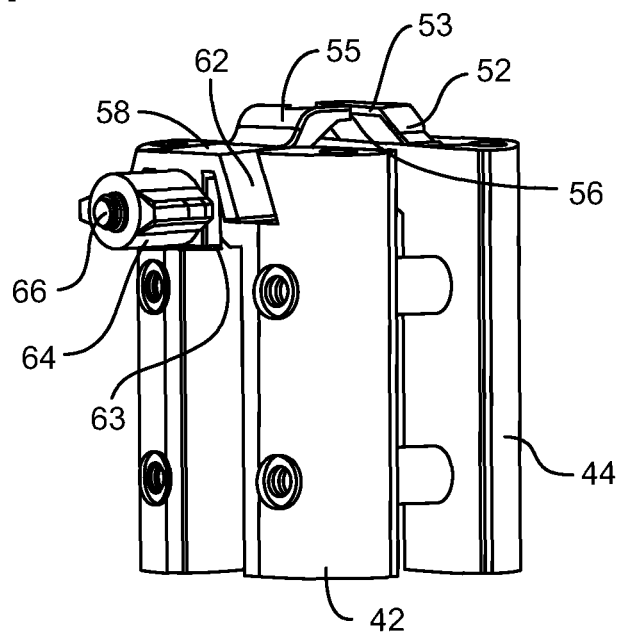
FIG. 5 is a side perspective view of the base assembly shown in FIG. 4.
Figure 6:
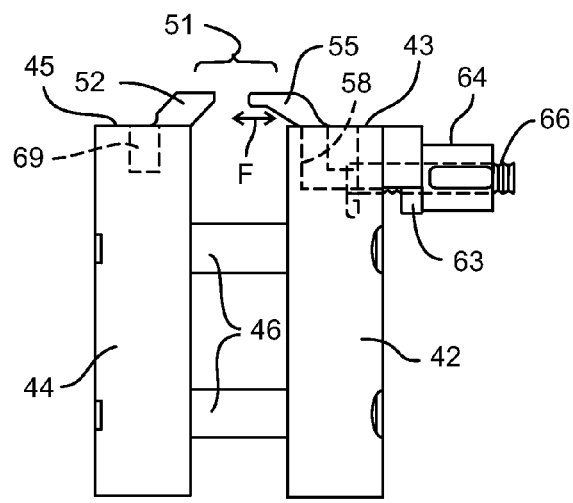
FIG. 6 is a side view of the base assembly shown in FIG. 4.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

For purposes of illustration, the preferred embodiment of the invention is described in connection with a shoulder prosthesis, and particularly the humeral component of the prosthesis. However, the inventive concepts disclosed herein can be used at other joints or bone interfaces of the body. The common feature among these alternative uses of the invention is that they include components that can assume a range of angular orientations relative to each other—angular orientations that must be duplicated from a trial implant or prosthesis to a final implant.

Referring now to FIG. 1 there is shown an exemplary embodiment of a shoulder prosthesis, generally designated 10. The shoulder prosthesis 10 includes a bone-engaging portion or stem 12 terminating in a neck 14, a spherical head 16, and a mounting assembly 18 mounting the head to the neck. The stem is configured for implantation within a bone, such as the humerus. The head 16 is configured to engage a mating joint component in the glenoid of the shoulder joint. The mounting assembly is "dialable", which means, in the context of the present invention, that the angular orientation of the head 16 relative to the stem 12 can be adjusted, preferably in multiple degrees of freedom. For instance, the head 16 can be adjusted in the medial-lateral direction ML and the superior-inferior direction SI or degree of freedom. This three-dimensional adjustability allows the implant to be configured to the particular patient anatomy.

The dialable mounting assembly provides a mounting interface between the stem neck 14 and the head 16. Preferably, the mounting assembly can be removably engaged to both the stem and the head. In certain implants, the angular adjustment feature is situated between the mounting assembly and the head. In other implants, the angular adjustment is effected between the mounting assembly and the stem. For purposes of explanation of the present invention, this latter adjustability feature is illustrated. In particular, the mounting assembly contemplates a tapered bore 20 defined in the neck 14 of the stem 12. This tapered bore defines a centerline which is used as a datum D, as explained in more detail below. The bore terminates in a concentric threaded bore 22.

The tapered bore receives a spherical joint 24 that is configured to be pressed into the tapered bore to form a locking engagement. This locking engagement can be enhanced by a mounting screw 30 that passes through a spherical seat 26 in the joint element and engages the threaded bore 22 in the stem. Tightening the screw into the bore pushes the spherical joint element 24 further into the tapered bore 20.

In the illustrated embodiment, the head 16 is engaged to the mounting assembly 18 by a taper-fit engagement. In particular, the mounting assembly defines a tapered bore 28 to receive a complementary tapered post 32 in a known manner. Alternatively, the head can incorporate the female locking component, as depicted in FIG. 2a. In this alternative configuration, the head 16' includes a tapered bore 32' that mates with the tapered exterior 28' of the mounting assembly 18'. The other elements of the construction of the dialable elements can be the same as illustrated in FIG. 2.

It is understood that the implant 10 as thus far described can be a trial implant used to size and orient the components of the implant. As is known, the associated bone is prepared to receive the stem 12 of the implant. Thus, for the illustrated shoulder implant, the humerus bone is resected, broached and reamed to receive the stem 12 with the neck 14 positioned in alignment with the glenoid component of the shoulder joint. The head 16 is selected to mate with the glenoid component of the joint, and the dialable mounting assembly 18 is adjusted to properly position the head on the neck within the shoulder joint. The implant components are locked together so their relative angular positions are fixed. The trial implant is then removed and the orientation recording and replication instrument of the present invention is used to duplicate the trial configuration in a final implant.

Figure 11:
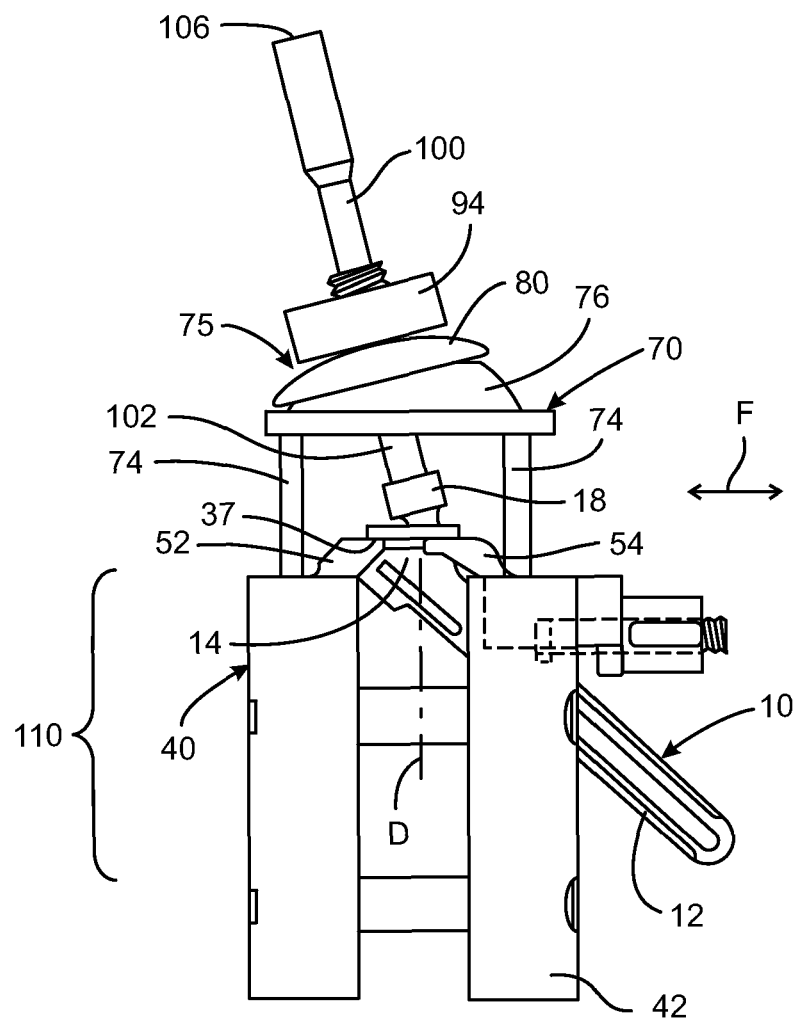
FIG. 11 is a side elevational view of a base assembly as depicted in FIG. 4 and a replication fixture as depicted in FIG. 9 forming the recording and replication instrument of one embodiment of the present invention.

In accordance with one aspect of the invention, the orientation recording and replication instrument 110 (see FIG. 11) comprises a base assembly 40 and a replication fixture 70 that is removably supported on the base assembly. Referring to FIGS. 4-8, details of the base assembly 40 will be discussed. In the illustrated embodiment, the base assembly includes two base halves 42 and 44 that are connected through a spacer 46. Mounting bolts 48 pass between the two halves and through the spacers to form a solid support base construction. At least the base half 42, and preferably both halves 42, 44, are generally U-shaped to define a slot 50. This slot 50 is sized to receive the stem 12 of an implant 10 passing therethrough when the implant is mounted within the base assembly, as depicted in FIG. 11.

The base assembly 40 includes an assembly that is configured to engage and clamp the neck 14 of an implant (trial or final). In one aspect of the invention, this assembly includes a self-centering clamp assembly 51 that is configured to clamp the implant to maintain a pre-determined datum in a pre-determined and repeatable orientation. The datum is a fixed location or axis on the implant that is common between the trial implant and the final implant, and is used to establish a known starting point for replicating the position of the dialable components of the implant. In the preferred embodiment, the datum is the central axis passing through the tapered bore 20 to which the dialable mounting assembly 18 mates. This datum is identified as the axis line D, as seen in FIGS. 2 and 11. As shown in FIG. 11, the base assembly 40 and clamp assembly 51 are preferably configured so that the datum D is vertically oriented when the implant 10 is supported by the base assembly. Of course, other pre-determined orientations of the datum D can be used, provided that the orientation is repeatable between all trial and final implants.

In order to ensure repeatability of the orientation of the datum D, the self-centering clamp assembly 51 contemplates clamp elements integrated with features on the implant itself. In particular, in accordance with the preferred embodiment, the clamp assembly includes a rear clamp element 52 with a clamping edge 53 configured to engage a rear clamping groove 37 (see FIGS. 2-3) defined in the neck 14. Similarly, the clamp assembly includes a centering clamp element 55 that includes a generally V-shaped clamping edge 56. This V-shaped edge is configured to engage angled grooves 35 defined in the neck 14 on the opposite side of the implant from the rear groove 37 (see, FIGS. 2-3). The grooves 35, 37 and the clamp elements 52, 55 are arranged so that the datum D is established at a pre-determined orientation when the implant is engaged by the clamp assembly 51. This pre-determined orientation of the datum is repeatable for every implant having similarly configured clamping grooves 35 and 37.

Figure 7:
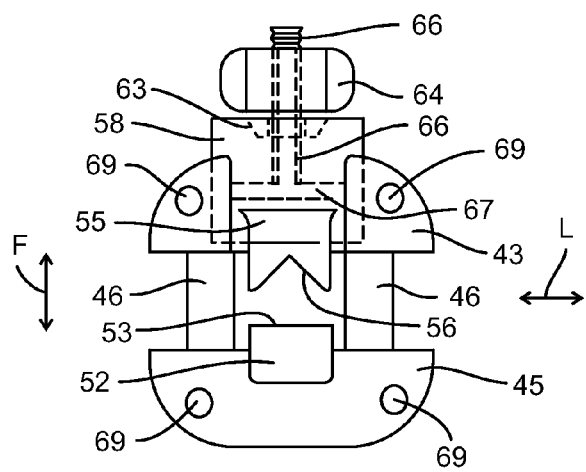
FIG. 7 is a top view of the base assembly shown in FIG. 4.

The V-shaped edge 56 of the centering clamp element 55 ensures that the neck 14 is laterally centered within the base assembly—i.e., the neck is centered along the axis L shown in FIG. 7. In accordance with the preferred embodiment, the rear clamp element 52 is fixed to the base half 44 so that the rear clamping edge 53 has a fixed position in along the fore-aft axis F (FIG. 7). Thus, the rear clamp element establishes the fore-aft position of the datum D when the rear clamping edge 53 is engaged within the rear groove 37 of the implant. In order to fix the implant within the clamp assembly, the centering clamp element 55 is slidably mounted within the base half 42 so that centering clamp element can move along the fore-aft axis F.

Figure 8:
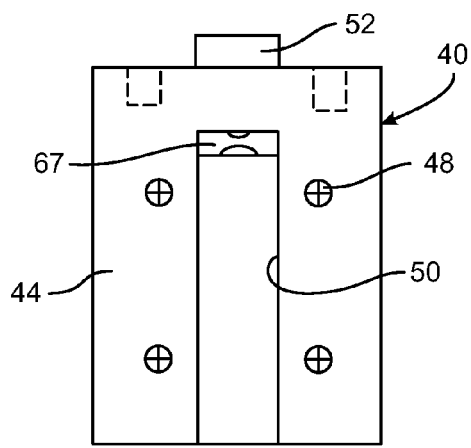
FIG. 8 is an end view of the base assembly shown in FIG. 4.

In the illustrated embodiment, the centering clamp element 55 is carried on a slidable carriage 58 that is disposed within a dovetail notch 60 defined in the base half 42, as seen best in FIG. 4. The carriage includes angled legs 62 that slide within the notch 60. A clamping nut 64 bears against a plate 63 extending from the legs 62 so that tightening the nut pushes the centering clamp element 55 toward the rear clamp element 52. The clamping nut is threaded onto a clamping post 66 that is mounted to the base half 42 by a drive plate 67 (FIG. 7-8). As the clamping nut 64 is rotated, it pushes against the drive plate 67 to push the carriage 58 along the dovetail notch 60 toward the implant neck 14 until the V-shaped clamping edge 56 engages the angled grooves 35 in the implant. As the clamping nut is tightened further, the V-shaped clamping edge manipulates the implant until the grooves 35 are centered relative to the clamping edge 56. At this point, the implant 10 is firmly held on the base assembly 40 by the self-centering clamp assembly 51 and the datum is automatically fixed in its pre-determined orientation so that the angular position of the dialable elements of the implant can be recorded.

The recording and replication feature of the invention is accomplished using the replication fixture 70 illustrated in FIGS. 9-10. The fixture includes a mounting platform 72 that is supported on the base assembly 40 by legs 74. In one feature, the legs fit within recesses 69 (FIGS. 4, 6-7) formed in the upper faces 43, 45 of the base halves 42, 44. The recesses 69 and legs 74 are accurately sized so that the mounting platform 72 assumes a pre-determined orientation relative to the base assembly 40, the clamp assembly 51, and more importantly the implant 10 supported by those two assemblies. Preferably, at least one of the legs 74 and associated recesses 69 are indexed so the legs are placed in the same orientation each time the fixture is removed and replaced on the base assembly. For example, one leg and recess can be differently sized form the other legs and recesses. In a specific embodiment, the indexed leg and recess have a smaller mating diameter than the other legs and recesses. As a further alternative, one leg and one recess can include a visual indicia or the leg and recess can include a key between the two components, such as a key and slot arrangement, to ensure that the fixture can be placed on the base assembly in only one orientation.

In the preferred embodiment, the replication fixture 70 is removably supported on the base assembly 40, which can facilitate positioning and removal of a trial or final implant within the base assembly. However, it is also contemplated that the replication fixture is essentially fixed to the base assembly—i.e., the base assembly and replication fixture are one-piece or fastened together. It is also contemplated that the overall configuration of the base assembly and replication fixture will depend upon the form of the implant being supported and replicated.

The replication fixture 70 utilizes an alignment tool 100 to interdigitate with the dialable feature of an implant mounted within the base assembly 40. The fixture further includes a locking assembly 75 that is operable to lock the angular orientation of the alignment tool to the fixture once it has been oriented relative to the implant 10, as described in more detail herein. The locking assembly 75 includes a dome 76 integrated into the mounting platform 72. The dome defines an opening 77 through which the alignment tool 100 extends. A spherical washer 80 rides on the dome 75 with its inner surface 81 in contact with the outer surface 76b of the dome. The washer also defines an opening 83 through which the alignment tool extends.

The alignment tool is carried by a guide member 85 having a spherical base 86 that nests with the dome 76. In particular, the guide base 86 includes an upper surface that bears against the inner surface 76a of the dome. A cylindrical post 90 projects from the spherical base 86 of the guide member. The post includes external threads 91 and an internal bore 92. The bore is sized to slidingly receive the alignment tool 100 therethrough. The opening 83 in the spherical washer 80 is sized to closely receive the post 90 therethrough. The opening 77 in the dome 76 is larger in size to permit angulation of the guide member 85 relative to the mounting platform 72.

In a specific embodiment, the post 90 of the guide member has an outer diameter of 0.875 inches, while the opening 83 in the washer has a diameter of 0.895 inches. On the other hand, the opening 77 in the dome has a diameter of 1.75 inches, or twice the diameter of the guide post, which will permit nested movement of the guide member 85 relative to the dome through a spherical angle of about ten degrees.

As shown in FIG. 10, the three components are successively assembled so that the dome 76 is sandwiched between the spherical washer 80 and the spherical base 86 of the guide member 85. This construction ensures controlled movement of the guide member and alignment tool relative to the fixed datum D of the implant 10 clamped within the base assembly 40. In other words, the construction only permits spherical angulation, while preventing transverse shifting of the tool relative to the datum.

The locking assembly 75 further includes a locking nut 94 with internal threads 95 to engage the external threads 91 of the guide post 90. The locking nut includes a face 96 that bears against a flat 82 of the spherical washer 80. When the nut is tightened it draws the washer and spherical base 86 of the guide member together with the dome 76 therebetween. When tightened enough, the nut 94 essentially locks the position of the guide member relative to the mounting platform 72 and to the base assembly 40, and ultimately to the datum D that was fixed relative to the base assembly when the implant was clamped in place by the self-centering clamp assembly 51.

It can be seen from the foregoing description that the two components of the instrument 110, namely the base assembly 40 and the replication fixture 70, work together to: a) establish a datum D on the implant that is fixed regardless of the implant; b) provides a movable guide member for an alignment tool; and c) provides means for locking the guide member once its position relative to the datum has been established by the alignment tool.

These features can be understood with reference to FIG. 11. Once the trial implant has been configured in situ it is removed from the patient and placed within the base assembly 40. In particular, the neck 14 of the implant is positioned within the self-centering clamp assembly in the orientation shown in FIG. 11. In this position, the stem 12 extends through the slot 50 in the base half 42 so the datum D can be vertically aligned in its fixed position. The head component can be removed, leaving the dialable mounting assembly 18 in the orientation achieved during trialing.

With the trial implant clamped in place, the replication fixture 70 is placed on the base assembly 40 with the legs 74 seated within the corresponding recesses 69 in the base halves 42, 44. The fixture 70 is thus positioned above the implant and more specifically above the dialable mounting assembly 18 (or the assembly 18' depicted in FIG. 2a). The alignment tool 100 is inserted through the bore 92 in the guide member post 90. The tool includes a guide shaft 102 with a diameter sized for close running fit within the bore 92. The tool 100 is provided with an insertion tip 103 at one end and a handle 105 at an opposite end. With the tool extending through the guide member, the handle 105 is manipulated until the tip 103 can be inserted into the tapered bore 28 in the mounting assembly 18. The tip 103 can be appropriately sized to form a tight, but removable, fit with the bore 28. Once the tip is firmly engaged with the mounting assembly, the locking assembly 75 can be manipulated to lock the position of the guide member relative to the mounting platform 72 and the datum D. Specifically, the nut 94 can be threaded onto the post 90 to tighten the spherical washer 80, dome 76 and spherical base 86 together. The alignment tool 100 is then removed.

The replication fixture can now be removed from the base assembly. The trial implant is removed from the clamping assembly and a final implant is positioned within the base assembly. It is understood that the final implant is substantially similar to the trial implant so that the datum D on the final implant will have the same orientation within the shoulder joint as the trial implant. Moreover, it is understood that the trial and final implants include the same configuration of the rear clamping groove 37 and the angled grooves 35 so that when any implant is fixed within the self-centering clamp assembly 51 the datum D consistently achieves the same orientation. Without this control, the trial orientation of the dialable components of the implant cannot be accurately replicated.

The final implant is lodged within the clamp assembly 51 in the same manner as the trial implant so that the datum D is in the vertical orientation shown in FIG. 11. The same replication fixture 70 is now placed onto the base assembly with the guide member 85 in the clamped position it was placed in when aligned with the trial implant. The same alignment tool 100 is introduced into the bore 92 of the guide member 85 and is manipulated until the insertion tip 103 engages the tapered bore 28 of the dialable mounting assembly. It is understood that the dialable component of the mounting assembly is loosely disposed within the tapered bore 20 in the neck 14 of the final implant. Thus, once the insertion tip contacts the tapered bore 28, manipulation of the alignment tool will alter the angular orientation of the dialable component. When the tip is fully seated within the bore 28, the position of the dialable component of the final implant exactly replicates the trialed position. The dialable component can then be fixed within the implant.

In accordance with the illustrated embodiment, the dialable component relies upon a taper fit between the dialable component and the tapered bore 20. In particular, the position of the dialable component is established when the spherical joint 24 is pressed into the tapered bore 28. In order to facilitate this press-fit engagement without sacrificing the replicated orientation, the present invention contemplates that the alignment tool 100 also serves as an impacting tool. Thus, the handle includes an impaction end 106 that can be struck by a mallet. The insertion tip 103 is hardened so that it can transmit the mallet impact into a force driving the spherical joint 24 into the tapered bore 20. Once the dialable mounting assembly is firmly seated, the alignment/impaction tool 100 can be retracted and the entire replication fixture 70 removed from the base assembly.

The fixation of the dialable component of the mounting assembly can be completed in accordance with the assembly—i.e., the mounting screw 30 can pass through the spherical seat 26, with the spherical head engaged within the sear, and into the threaded bore 22 of the neck 14. In addition, the head 16 can be added to the implant while the implant is still held within the clamp assembly 51. Once the final implant has been assembled it can be removed from the base assembly 40 and implanted within the patient's shoulder joint. It should be understood that the present invention can be utilized with other means for fixing or engaging the dialable components other than the taper-fit or press-fit engagement described above. Moreover, it is understood that the impaction aspect of the invention can be utilized on other forms of fixation, such as interdigitating elements or teeth, to complete the assembly. In addition, the engagement can be by threading or similar mechanism, in which case the impaction tool would be appropriately configured to accomplish the threaded engagement.

The instrument 110 provides s simple and easily managed device for replicating the orientation of dialable components of an orthopaedic implant. In accordance with the preferred embodiment, the implant itself incorporates landmark features that are fixed relative to a pre-determined datum and that are keyed on to clamp and support the implant with the datum in a known and repeatable orientation. In other words, in accordance with the illustrated embodiment, the neck 14 of the implant 10 (both trial and final) is provided with clamping grooves 35 and 37. Moreover, the clamping assembly includes clamp elements 52 and 55 that are configured to lodge within these corresponding grooves. It is understood, however, that the implant can be provided with alternative landmark features and that the clamp elements can be appropriately configured to key on the alternative landmarks. Furthermore, the clamp elements can be configured to key on existing fixed and repeatable landmark features that are integrated into the existing implant design. It is important that the clamp assembly be able to achieve repeatable positioning of the same datum on any implant, whether trial or final.

The illustrated embodiment also contemplates one type of dialable component for a mounting assembly to mount a humeral head to the stem of a humeral implant. Of course, other implants include other types of dialable components of the implant with other types of clamping mechanisms to fix the position of the dialable component. For instance, in certain embodiments, the dialable component is integrated into the humeral head itself—e.g., the spherical joint 24 is integral with the underside of the head 16. If this modified head is configured to accept a mounting screw, such as the screw 30, then the head will include a bore, like the bore 28, that can be engaged by the alignment tool 100 in the manner described above.

In other embodiments, the dialable component of the mounting assembly may not be configured to mate with the insertion tip 103 of the alignment tool 100 described above. It is contemplated that the working end of the alignment tool 100 be configured as necessary to engage the dialable component when fixed within a trial implant and when loosely situated within a final implant. For example, the dialable component may include a stem and the working end of the alignment tool can include a bore configured for a tight fit with the stem.

The alignment tool 100 can also include an alignment groove 108 defined in its working end. The alignment groove can mate with a corresponding key in the dialable mounting assembly. The key and groove can be used to locate a rotational angle or to perform a rotating driving function, such as to fix a threaded engagement.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A system for preparing an implant for implantation, the system comprising:
    a trial implant including a first dialable component and a datum;
    a final implant including a second dialable component; and
    an instrument including (i) a base assembly configured to support the trial implant so that the datum is in a predetermined orientation, (ii) a fixture supported on the base assembly, the fixture including a domed element, and an alignment tool configured to engage the first dialable component when the trial implant is supported by said base assembly, and (iii) a locking assembly including a guide member defining a spherical surface for nested engagement with said domed element, the locking assembly configured to record the angular orientation of said alignment tool relative to said fixture with said alignment tool engaged with the first dialable component, and to replicate the recorded angular orientation with the alignment tool and the second dialable component.

2. The system of claim 1, wherein the second dialable component comprises:
    a spherical portion configured to be mounted to a stem portion of the final implant by engaging a tapered bore; and
    a tapered post configured to engage a tapered bore within a head component.

3. The system of claim 2, wherein the alignment tool is configured as an impact tool to transmit an impaction force to the second dialable component when the recorded angular orientation is replicated with the alignment tool and the second dialable component so that the second dialable component is impacted into a locking engagement within the tapered bore.

4. The system of claim 3, wherein the tapered bore is defined within a neck portion of the stem portion.

5. The system of claim 4, further comprising:
    a mounting screw configured to engage a spherical seat within the second dialable component, and to engage a threaded bore extending from the tapered bore.

6. The system of claim 1, wherein the base assembly includes a clamp assembly configured to clamp a stem portion of the final implant.

7. The system of claim 6, wherein the clamp assembly is configured to center the final implant relative to the base assembly in at least two degrees of freedom.

8. The system of claim 7, wherein:
    the stem portion includes a pair of angled groove portions; and
    the clamp assembly is configured to engage the pair of angled groove portions.

9. The system of claim 8, wherein the clamp assembly includes a pair of angled clamping edge portions configured to engage the pair of angled groove portions.

10. The system of claim 9, wherein:
    the stem portion further includes an opposing clamping groove portion spaced apart from the pair of angled groove portions; and
    the clamp assembly is configured to engage the opposing clamping groove portion.

11. The system of claim 10, wherein the clamp assembly further comprises:
    a movable carriage configured to move one of the pair of angled clamping edge portions and an opposing clamping edge portion toward the other of the pair of angled clamping edge portions and the opposing clamping edge portion.

12. The system of claim 11, wherein the clamp assembly further comprises:
   a clamping nut engaged with a threaded clamping post such that rotation of the clamping nut in a first direction forces the movable carriage to move the one of the pair of angled clamping edge portions and an opposing clamping edge portion toward the other of the pair of angled clamping edge portions and the opposing clamping edge portion.

13. The system of claim 10, wherein the fixture is removably supported on the base assembly in the predetermined orientation using a keyed relationship between the fixture and the base assembly.

14. The system of claim 13, wherein the locking assembly is configured to permit removal of the alignment tool while the locking assembly is locked.

15. The system of claim 10, wherein:
   the fixture includes a fixed domed element defining a domed element opening; and
   the locking assembly includes a guide member with (i) a base portion configured to abut an inner surface of the domed element, and (ii) a post configured to extend from the base portion through the domed element opening.

16. The system of claim 15, wherein:
   the post defines a post opening sized to receive at least a portion of the alignment tool therethrough.

17. The system of claim 16, wherein:
   the post includes a threaded portion; and
   the locking assembly further includes a nut configured to engage the threads.

18. The system of claim 17, wherein:
   the locking assembly further includes a washer configured to be positioned about the post and abut an outer surface of the domed element.

19. The system of claim 18, wherein:
   the base portion includes an arcuate surface shaped complementary to the inner surface of the domed element; and
   the washer includes an arcuate surface shaped complementary to the outer surface of the domed element.

20. The system of claim 10, wherein:
   the second dialable component includes (i) a spherical portion configured to be mounted to a stem portion of the final implant by engaging a tapered bore, and (ii) a tapered post configured to engage a tapered bore within a head component; and
   the alignment tool is configured as an impact tool to transmit an impaction force to the second dialable component when the recorded angular orientation is replicated with the alignment tool and the second dialable component so that the second dialable component is impacted into a locking engagement within the tapered bore.

\* \* \* \* \*